United States Patent [19]

Blair et al.

[11] Patent Number: 5,221,624
[45] Date of Patent: Jun. 22, 1993

[54] DNA ENCODING (LYS[46], ASP[97], ASP[113]) AND (LYS[46], ASP[113], ASP[137]) THAUMATIN I POLYPEPTIDES

[75] Inventors: Lindley C. Blair, Los Angeles; Raju K. Koduri, LaJolla; Jar-How Lee, Palos Verdes Estates; Joachim L. Weickmann, Los Angeles, all of Calif.

[73] Assignee: International Genetic Engineering, Inc., Santa Monica, Calif.

[21] Appl. No.: 407,416

[22] Filed: Sep. 14, 1989

Related U.S. Application Data

[63] Continuation-in-part of Ser. No. 268,702, Nov. 8, 1988, abandoned.

[51] Int. Cl.[5] .................. C12P 21/00; C12N 15/00; C12N 15/29; C12N 15/70; C12N 15/81
[52] U.S. Cl. .................. 435/252.33; 435/69.1; 435/172.3; 435/243; 435/256; 435/320.1; 536/23.6; 935/10
[58] Field of Search .... 435/69.1, 172.3, 252.3-252.35, 435/320.1, 243, 255, 256; 536/27; 935/10, 72-75

[56] References Cited

U.S. PATENT DOCUMENTS 4,766,205 8/1988 Ghosh-Dastidar ............. 530/402
4,771,000 9/1988 Verrips et al. ............. 435/69.1

FOREIGN PATENT DOCUMENTS 8703008 5/1987 World Int. Prop. O. .

OTHER PUBLICATIONS

Broach, Methods in Enzymology, 101:307-325.
Edens et al., Gene, 18, 1-12 (1982).
Fieschko, et al., Biotech. & Bioeng., vol. XXIX, pp. 1113-1121, John Wiley & Sons (1987).
Higginbotham, et al., Flavor Potentiating Properties of Talin Sweetener (Thaumatin). The Quality of Foods and Beverages, Academic Press, New York, 91-111 (1981).
Higginbotham, et al., Sensory Properties of Foods (Birch, et al., eds.), London: Applied Sicences, pp. 129-149 (1977).
Huang, et al., Biochemistry, (1987), 26:8242-8246.
Iyengar, et al., Eur. J. Biochem., 96, 193-204 (1979).
Kendall, et al., Nature, 321, 706-708 (1986).
Larson-Powers and Pangborn, J. Food Science, 43(1), 41-46 (1978).
Miyada, et al., Gene, (1982), 17:167-177.
Oliver, Ann. Rev. Microbiol., 39, 615-48 (1985).
Sanger, et al., Proc. Natl. Acad. Sci. USA (1977), 74:5463-5467.
Sjostrom, et al., The EMBO Journal, 6, 823-831 (1987).
Swartz, et al., Food Technology, vol. 31, 51-67 (1977).
van der Wel, et al., Chemical Senses and Flavor, 2, 211-218 (1976).
Von Heijne, European J. Biochem., 133, 17-21 (1983).

*Primary Examiner*—James Martinell
*Attorney, Agent, or Firm*—Marshall, O'Toole, Gerstein, Murray & Bicknell

[57] ABSTRACT

Genes are disclosed which are capable of directing the synthesis in a selected host microorganism of thaumatin I polypeptides having improved taste characteristics characterized by having the amino acid sequence of natural thaumatin I including a lysine amino acid residue substituted for asparagine in the 46th position from the amino terminal end, an aspartate amino acid residue substituted for asparagine in the 113th position from the amino terminal end and an aspartate amino acid residue substituted for lysine at either the 97th or 137th residue from the amino terminal end.

16 Claims, 2 Drawing Sheets

DNA ENCODING (LYS$^{46}$, ASP$^{97}$, ASP$^{113}$) AND (LYS$^{46}$, ASP$^{113}$, ASP$^{137}$) THAUMATIN I POLYPEPTIDES

This application is a continuation-in-part of U.S. patent application Ser. No. 07/268,702 filed Nov. 8, 1988, now abandoned the disclosure of which is herein incorporated by reference.

BACKGROUND

The present invention relates generally to the manipulation of genetic materials and more particularly to the manufacture of specific DNA sequences useful in recombinant procedures to secure the production of improved variants of a polypeptide identified as natural thaumatin I.

Thaumatin is an extremely sweet-tasting protein produced in the arils of the fruit of the African shrub *Thaumatococcus daniellii* Benth. The fruit traditionally has been used in West Africa as a sweetener of palm wine, corn bread, and sour fruit. Thaumatin, which is about 5,000 times sweeter than sucrose on a weight basis, is produced in at least five forms: thaumatins I, II, a, b and c. These proteins, named in the order of elution from an ion exchange column [Higginbotham, et al., in *Sensory Properties of Foods* (Birch, et al., eds.), London: Applied Sciences, pp. 129-149 (1977)], have molecular weights of approximately 22 kilodaltons. Thaumatins I and II are nearly identical proteins, each consisting of a single unmodified polypeptide chain, 207 amino acid residues in length.

Thaumatin is a non-toxic, low-calorie and noncariogenic protein which elicits profound sweet taste responses. These properties suggest a stable interaction between the proteins and human taste receptors. Therefore, thaumatin has potential for use as a sugar substitute, food additive, a sweetness receptor probe and a tool for further elucidation of the taste response.

A plentiful supply of pure thaumatin is required to utilize the protein as a possible food additive and research tool. Because the thaumatin plant requires a tropical climate and insect pollination for successful fruit propagation, there are considerable difficulties involved in greenhouse cultivation of the fruit.

Iyengar disclosed an amino acid sequence for thaumatin I which is shown in Table 1 below [Iyengar, et al., *Eur. J. Biochem.*, 96, 193-204 (1979)].

TABLE 1

```
                                      1                                              10
                       NH2—Ala—Thr—Phe—Glu—Ile—Val—Asn—Arg—Cys—Ser—Tyr—Thr—Val—

20
                       Trp—Ala—Ala—Ala—Ser—Lys—Gly—Asp—Ala—Ala—Leu—Asp—Ala—Gly—

30                                              40
                       Gly—Arg—Gln—Leu—Asn—Ser—Gly—Glu—Ser—Trp—Thr—Ile—Asn—Val—

50
                       Glu—Pro—Gly—Thr—Asn—Gly—Gly—Lys—Ile—Trp—Ala—Arg—Thr—Asp—

60
                       Cys—Tyr—Phe—Asp—Asp—Ser—Gly—Ser—Gly—Ile—Cys—Lys—Thr—Gly—

70                                              80
                       Asp—Cys—Gly—Gly—Leu—Leu—Arg—Cys—Lys—Arg—Phe—Gly—Arg—Pro—

90
                       Pro—Thr—Thr—Leu—Ala—Glu—Phe—Ser—Leu—Asn—Gln—Tyr—Gly—Lys—

100                                           110
                       Asp—Tyr—Ile—Asp—Ile—Ser—Asn—Ile—Lys—Gly—Phe—Asn—Val—Pro—

120
                       Met—Asn—Phe—Ser—Pro—Thr—Thr—Arg—Gly—Cys—Arg—Gly—Val—Arg—

130
                       Cys—Ala—Ala—Asp—Ile—Val—Gly—Gln—Cys—Pro—Ala—Lys—Leu—Lys—

140                                           150
                       Ala—Pro—Gly—Gly—Gly—Cys—Asn—Asp—Ala—Cys—Thr—Val—Phe—Gln—

160
                       Thr—Ser—Glu—Tyr—Cys—Cys—Thr—Thr—Gly—Lys—Cys—Gly—Pro—Thr—

170                                           180
                       Glu—Tyr—Ser—Arg—Phe—Phe—Lys—Arg—Leu—Cys—Pro—Asp—Ala—Phe—

190
                       Ser—Tyr—Val—Leu—Asp—Lys—Pro—Thr—Thr—Val—Thr—Cys—Pro—Gly—

200                              207
                       Ser—Ser—Asn—Tyr—Arg—Val—Thr—Phe—Cys—Pro—Thr—Ala—COOH
```

The amino acid sequence for thaumatin II has been deduced from its nucleotide sequence [Edens, et al., *Gene*, 18, 1-12 (1982)] and a gene for thaumatin II has been cloned from messenger RNA-derived cDNA. The five amino acids in the thaumatin II sequence which differ from the thaumatin I sequence above are the following: lysine instead of asparagine at residue 46; arginine instead of serine at residue 63; arginine instead of lysine at residue 67; glutamine instead of arginine at residue 76; and aspartic acid instead of asparagine at residue 113. Sequence analysis also indicated that thaumatin II is initally translated as a precursor form, preprothaumatin, with both a 22 residue amino-terminal extension and an acidic, six-amino acid carboxy terminal tail. The amino terminal peptide was postulated as a secretion signal based on its hydrophobic character and a compartmentalization role was hypothesized for the carboxy terminal extension.

The Edens, et al. reference cited above notes that a polypeptide having the native sequence of preprothaumatin II has been microbially produced. More specifically, the reference and Verrips, et al., U.S. Pat. No. 4,771,000 disclose cDNA sequences coding for native mature thaumatin II and preprothaumatin II and also disclose cloning vehicles comprising the DNA sequences for use in transformation in microorganisms.

In co-owned and copending U.S. patent application Ser. No. 540,634 filed Oct. 11, 1983, the disclosure of which is herein incorporated by reference, techniques for the synthesis of manufactured genes coding for the amino acid sequence of thaumatin I as identified by Iyengar, et al. were disclosed, as were DNA microorganism transformation vectors, fusion genes, transformed microorganisms, and processes for expressing the manufactured gene and for securing the polypeptide product produced thereby. Specific manufactured genes of the application incorporated a number of codons "preferred" for expression in yeast host cells.

In co-owned and copending U.S. patent application Ser. No. 189,250, a continuation of Ser. No. 797,474 filed Nov. 13, 1985, the disclosure of which is hereby incorporated by reference, polypeptides and genes for their synthesis were disclosed having the amino acid sequence of [Asp$^{113}$] thaumatin I and [Lys$^{46}$, Asp$^{113}$] thaumatin I, i.e., containing the continuous sequence of amino acid residues of natural thaumatin I as reported by Iyengar, et al. except for an aspartate amino acid residue substituted for asparagine in the 113th position from the amino terminal end of the polypeptide and optionally a lysine amino acid residue substituted for asparagine in the 46th position. Those polypeptides could be folded to a sweet conformation using an in vitro procedure. Recombinant produced thaumatin I having the published Iyengar, et al. amino acid sequence was not sweet and could not be folded to a sweet conformation.

While the recombinant produced [Asp$^{113}$] and [Lys$^{46}$, Asp$^{113}$] thaumatin I polypeptides constitute improvements over the art, they share with plant derived thaumatin taste characteristics which may limit their use in some food products. Most significant of these characteristics is a lingering aftertaste unlike that exhibited by sugar (sucrose).

Of interest to the present invention is the disclosure of van der Wel, et al., Chemical Senses and Flavor, 2, 211-218 (1976). This reference discloses experiments in which lysine residues in thaumatin I were chemically modified by acetylation with acetic anhydride and by reductive methylation. At least four acetylated thaumatins were obtained with either one, two, three or four acetylated amino groups. In addition, a methylated thaumatin was produced having six dimethyl lysine residues and one monomethyl lysine residue. While the methylated thaumatin with seven modified lysine residues had a sweetness intensity practically equal to that of the original thaumatin, the sweetness intensity of the acetylated thaumatins decreased with the increasing number of acetylated amino groups. The sweet taste sensation disappeared completely when four acetylated lysine residues were introduced into the molecule. The reference suggested the possibility that a correlation between net charge and the sweetness intensity of the molecule may exist.

Of interest to another aspect of the present invention are references relating to polypeptide secretion signal sequences. Von Heijne, European J. Biochem., 133, 17-21 (1983), discloses a variety of eukaryotic signal sequences and notes that signal sequences typically contain two different, independent signals. The first signal is said to be in the form of a hydrophobic core while the second one is said to confer processing specificity. Oliver, Ann. Rev. Microbiol., 39, 615-48 (1985), relates to protein secretion in *Escherichia coli* and discloses a variety of bacterial secretion signals which are characterized as including three conserved features including (a) a positively charged amino terminus, (b) a hydrophobic core and (c) a highly conserved sequence adjacent to the processing site.

Kendall, et al., Nature, 321, 706-708 (1986), discloses the use of site-directed mutagenesis to produce a mutant signal sequence containing nine consecutive leucine residues in the hydrophobic core segment Sjostrom, et al., The EMBO Journal, 6, 823-831 (1987), relates to analysis of *E. coli* secretion signal sequences and discloses the presence of lysine residues in the amino terminal end of the sequence for a high number of *E. coli* signal sequences. Sjostrom, et al. note, however, that the signal peptides of eukaryotes rarely have sequence homologies.

SUMMARY OF THE INVENTION

The present invention provides purified and isolated DNA sequences capable of directing synthesis in a selected host microorganism of [Lys$^{46}$, Asp$^{97}$, Asp$^{113}$] thaumatin I and [Lys$^{46}$, Asp$^{113}$, Asp$^{137}$] thaumatin I containing the continuous sequence of amino acid residues of natural thaumatin I as reported by Iyengar, et al. except for a lysine amino acid residue substituted for asparagine in the 46th position from the amino terminal end of the polypeptide, an aspartic acid residue substituted for asparagine in the 113th position and either aspartic acid for lysine in the 97th position or aspartic acid for lysine in the 137th position. In preferred forms of the genes, the base sequences include one or more codons specifying the same amino acid on the basis of preferential expression characteristics of the codon in a projected host microorganism, e.g., *E. coli*, *Saccharomyces cerevisiae*. Other preferred forms of manufactured genes include those wherein: (1) a codon specifies an additional amino acid in the polypeptide synthesized (e.g., an initial methionine residue) which facilitates direct expression in *E. coli* microorganisms and/or yeast microorganisms; or (2) at least one termination codon at the end of the manufactured gene to insure proper termination of the polypeptide.

In practice of the invention to generate polypeptide products, DNA sequences, including manufactured genes, are inserted into a viral or circular plasmid DNA vector to form a hybrid vector and the hybrid vectors are employed to transform host microorganisms such as bacteria (e.g., *E. coli*) or yeast cells (e.g., *S. cerevisiae*). Vectors may also be supplied with appropriate promoter/regulator DNA sequences, allowing for controlled expression in the host microorganism. The transformed microorganisms are thereafter grown under appropriate nutrient conditions and express the polypeptide products of the invention.

The invention also provides novel DNA sequences encoding improved yeast secretion signal sequences which decrease the lag time required for transformants to appear for recombinant produced polypeptides such as thaumatin. In addition, the invention further provides preferred mutagenized host cells for expression and secretion of the thaumatin proteins of the invention.

The novel [Lys$^{46}$, Asp$^{97}$, Asp$^{113}$] and [Lys$^{46}$, Asp$^{113}$, Asp$^{137}$] thaumatin I polypeptides provide novel taste characteristics, particularly with respect to reduced longevity of sweet aftertaste. This invention teaches the importance of the 97th and 137th amino acid residues to the biological properties such as taste characteristics of the thaumatin I molecule. It is expected that additional thaumatin I polypeptides having improved taste characteristics can be produced by substitution of amino acids other than aspartic acid for lysine at either position 97 or 137. Other aspects and advantages of the present invention will be apparent upon consideration of the following detailed description thereof.

DETAILED DESCRIPTION OF THE INVENTION

EXAMPLE 1

Figure 1:
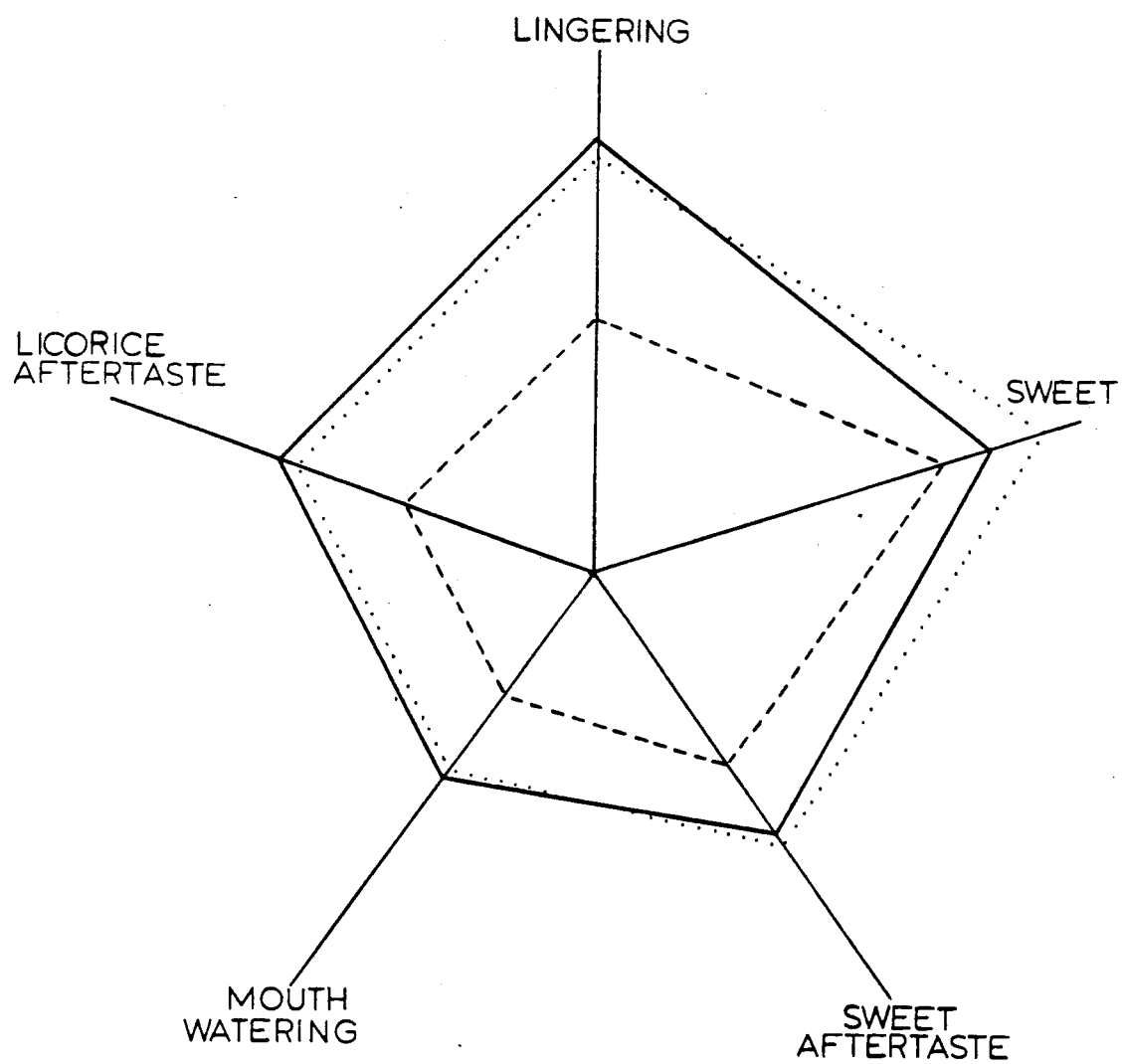
FIG. 1 is a depiction of the relative taste qualities of [Lys$^{46}$, Asp$^{97}$, Asp$^{113}$] and [Lys$^{46}$, Asp$^{113}$, Asp$^{137}$] thaumatin I polypeptides and plant derived thaumatin.

In this example, plasmids pING152T encoding [Lys$^{46}$, Asp$^{113}$, Asp$^{137}$] thaumatin I and pING323T encoding [Lys$^{46}$, Asp$^{97}$, Asp$^{113}$] thaumatin I were constructed from plasmids pKS6 and M13mp10-thaumatin, the constructions of which are described in co-owned and copending U.S. patent application Ser. No. 189,250 filed May 2, 1988, the disclosure of which is hereby incorporated by reference, and pING58T, the construction of which is described in published international application No. US/PCT86/02443 corresponding to, copending U.S. patent application Ser. No. 797,477 filed Nov. 13, 1985, the disclosure of which is hereby incorporated by reference.

Plasmid pKS6, which contains the 218 bp PGK promoter and encodes for a [Lys$^{46}$, Asp$^{113}$] thaumatin I polypeptide, was cut with BamHI and XhoI and the 850 base pair PGK promoter-thaumatin fragment was ligated to BamHI and XhoI cut M13MP10-thaumatin to form plasmid M13-KS6. The single-stranded phage DNA was prepared from M13-KS6 and used as template for site-directed mutagenesis.

Two oligonucleotides, 5'-GAGCCTTAAGGT-CAGCTGGACAT-3' for changing Lys$^{137}$ to Asp and 5'-GATGTAGTCGTCACCGTATTG-3' for changing Lys$^{97}$ to Asp were annealed to M13-KS6, separately, and site-directed mutagenesis was performed as described in Miyada, et al., Gene, (1982), 17:167–177. The same oligonucleotides used for mutagenesis were used as probes to screen for positive plaques. Positive plaques were sequenced by the chain termination reaction (Sanger, et al., Proc. Natl. Acad. Sci. USA, (1977), 74:5463–5467) and the desired changes were confirmed. One positive plaque from each mutagenesis was picked.

Double-stranded replicated-form DNA was prepared, cut with BamHI and XhoI, ligated to BamHI and XhoI cut pING58T to form pING152T [Lys$^{137}$ to Asp$^{137}$] and pING323T [Lys$^{97}$ to Asp$^{97}$]. These two constructs upon transformation into yeast strain BB29-lc produced intracellular [Lys$^{46}$, Asp$^{113}$, Asp$^{137}$] thaumatin I and [Lys$^{46}$, Asp$^{97}$, Asp$^{113}$], thaumatin I, respectively. The thaumatin polypeptides were purified from yeast cell extracts as described in co-owned and copending U.S. Pat. No. 4,766,205, the disclosure of which is hereby incorporated by reference, and each refolded to a sweet form.

EXAMPLE 2

In this example, plasmids pING152CVS and pING323CVS were constructed and separately transformed into yeast strains. A yeast secretion vector, plasmid pING804CVS, which contains the 220 bp PGK promoter, the SUC2 yeast invertase signal sequence, the structural sequence for [Lys$^{46}$, Asp$^{113}$] thaumatin I from which a 138 base pair deletion has been made and the PGK terminator on a medium copy yeast vector CV20 (YEp20, ATCC 37059, Broach, Methods in Enzymology, 101:307–325) was used as the base vector for constructing the YT152 and YT323 secretion vectors. The reason for choosing pING804CVS as a base vector is because it generates a smaller BglII - XhoI fragment and can be easily distinguished from the full size BglII - XhoI fragment of the YT152 and YT323 genes. Plasmids pING152T and pING323T were cut with BglII and XhoI and the 485 bp partial thaumatin genes ligated to BglII and XhoI cut pING804CVS to generate pING152CVS and pING323CVS, respectively.

Plasmids pING152CVS and pING323CVS were transformed into yeast strain AH7 (MATα leu2-3), (obtained from the laboratory of Gerald Fink, Whitehead Institute of Cancer Research) separately. Leu+ transformants were grown in SD-leu for 4 days and samples taken for radioimmunoassay. The secretion level of YT152 or YT323 was determined to be approximately 0.4 μg/ml.

EXAMPLE 3

As an alternative means of producing vectors encoding the thaumatin polypeptides of the present invention, it is well within the skill in the art to synthesize using commercially available devices entire nucleotide sequences encoding the amino acid sequences of the thaumatin polypeptides of the invention along with suitable promoter, secretion signal and terminator sequences. Cassettes comprising such sequences may be provided at their 5' and 3' ends with nucleotides duplicative of restriction sites in order that they may be readily inserted into suitable plasmids.

For example, provided below in Tables 2 and 3 are nucleotide sequences of DNA cassettes encoding the pING152CVS sequence comprising PGK promoter - SUC2 signal sequence - [Lys$^{46}$, Asp$^{113}$, Asp$^{137}$] thaumatin I -PGK terminator (Table 2) and the pING323CVS sequence comprising PGK promoter - SUC2 signal sequence - [Lys$^{46}$, Asp$^{97}$, Asp$^{113}$] thaumatin I - PGK terminator (Table 3). These sequences also include "sticky ends" to a BamHI site at the 5' end and a SalI site at the 3' end and when inserted into publicly available plasmid CV20 (YEp20, ATCC 37059) opened with the BamHI and SalI restriction enzymes produce alternatively pING152CVS and pING323CVS.

TABLE 2 pING152CVS Sequence

```
         10         20         30         40         50
GGATCCCGAC TCTTTTCTTC TAACCAAGGG GGTGGTTTAG TTTAGTAGAA
CCTAGGGCTG AGAAAAGAAG ATTGGTTCCC CCACCAAATC AAATCATCTT
BamHI 60         70         80         90        100
CCTCGTGAAA CTTACATTTA CATATATATA AACTTGCATA AATTGGTCAA
GGAGCACTTT GAATGTAAAT GTATATATAT TTGAACGTAT TTAACCAGTT 110        120        130        140        150
TAGCAGAAAT AGATATTTGG TCTTTTCTAA TTCGTAGTTT TTCAAGTTCT
ACGTTCTTTA TCTATAAACC AGAAAAGATT AAGCATCAAA AAGTTCAAGA 160        170        180        190        200
TAGATGCTTT CTTTTTCTCT TTTTTACAGA TCATCAAGGA AGTAATTATC
ATCTACGAAA GAAAAAGAGA AAAAATGTCT AGTAGTTCCT TCATTAATAG

PGK Promoter<——|——>SUC2 Signal Sequence
        210        220        230        240        250
TACTTTTTAC AACAAATATA AAAACAAGAT CATGCTTTTG GAAGCTTTCC
ATGAAAAATG TTGTTTATAT TTTTGTTCTA GTACGAAAAC GTTCGAAAGG <——|——>YT152
        260        270        280        290        300
TTTTCCTTTT GGCTGGTTTT GCAGCCAAAA TATCTGCCGC TACCTTCGAA
AAAAGGAAAA CCGACCAAAA CGTCGGTTTT ATAGACGGCG ATGGAAGCTT 310        320        330        340        350
ATCGTTAACA GATGTTCTTA CACTGTTTGG GCTGCTGCTT CCAAGGGTGA
TAGCAATTGT TTACAAGAAT GTGACAAACC CGACGACGAA GGTTCCCACT 360        370        380        390        400
CGCTGCTTTG GACGCCGGTG GTAGACAATT GAACTCTGGT GAATCCTGGA
GCGACGAAAC CTGCGGCCAC CATCTGTTAA CTTGAGACCA CTTAGGACCT 410        420        430        440        450
CCATCAACGT CGAACCAGGT ACCAAGGGTG CTAAGATCTG GCTAGAACC
GGTAGTTGCA GCTTGGTCCA TGGTTCCCAC CATTCTAGAC CCGATCTTGG
                                     BglII 460        470        480        490        500
GACTGTTACT TCGATGACTC TGGTTCCGGT ATCTGTAAGA CTGGTGACTG
CTGACAATGA AGCTACTGAG ACCAAGGCCA TAGACATTCT GACCACTGAC 510        520        530        540        550
TGGTGGTTTG TTGAGATGTA AGAGATTCGG TAGACCACCA ACCACTTTGG
ACCACCAAAC AACTCTACAT TCTCTAAGCC ATCTGGTGGT TGGTGAAACC 560        570        580        590        600
CTGAATTCTC TTTGAACCAA TACGGTAAGG ACTACATCGA TATCTCCAAC
GACTTAAGAG AAACTTGGTT ATGCCATTCC TGATGTAGCT ATAGAGGTTG 610        620        630        640        650
ATCAAGGGTT TCAACGTTCC AATGGACTTC TCTCCAACCA CTAGAGGTTG
TAGTTCCCAA AGTTGCAAGG TTACCTGAAG AGAGGTTGGT CATCTCCAAC 660        670        680        690        700
TAGAGGCGTC AGATGTGCTG CTGACATCGT TGGTCAATGT CCAGCTGACC
ATCTCCGCAG TCTACACGAC GACTGTAGCA ACCAGTTACA GGTCGACTGG
                                               Asp¹³⁷

710        720        730        740        750
TTAAGGCTCC AGGTGGTGGT TGTAACGACG CTTGTACCGT TTTCCAAACT
AATTCCGAGG TCCACCACCA ACATTGCTGC GAACATGGCA AAAGGTTTGA 760        770        780        790        800
TCCGAATACT GTTGTACCAC TGGTAAGTGT GGTCCAACCG AATACTCTAG
AGGCTTATGA CAACATGGTG ACCATTCACA CCAGGTTGGC TTATGAGATC 810        820        830        840        850
ATTCTTCAAG AGATTGTGTC CAGACGCTTT CTCCTACGTC TTGGACAAGC
TAAGAAGTTC TCTAACACAG GTCTGCGAAA GAGGATGCAG AACCTGTTCG 860        870        880        890        900
CAACTACCGT CACTTGTCCA GGTTCTTCCA ACTACAGAGT TACCTTCTGT
GTTGATGGCA GTGAACAGGT CCAAGAAGGT TGATGTCTCA ATGGAAGACA
```

TABLE 2-continued
pING152CVS Sequence

```
            YT152◄──┼──►PGK Terminator
      910        920        930        940        950
CCAACTGCCT AATGACTCGA GGGATCTCCC ATGTCTCTAC TGGTGGTGGT
GGTTGACGGA TTACTGAGCT CCCTAGAGGG TACAGAGATG ACCACCACCA
                XhoI 960        970        980        990       1000
GCTTCTTTGG AATTATTGGA AGGTAAGGAA TTGCCAGGTG TTGCTTTCTT
CGAAGAAACC TTAATAACCT TCCATTCCTT AACGGTCCAC AACGAAAGAA 1010       1020       1030       1040       1050
ATCCGAAAAG AAATAAATTG AATTGAATTG AAATCGATAG ATCAATTTTT
TAGGCTTTTC TTTATTTAAC TTAACTTAAC TTTAGCTATC TAGTTAAAAA 1060       1070       1080       1090       1100
TTCTTTTCTC TTTCCCCATC CTTTACGCTA AAATAATAGT TTATTTTATT
AAGAAAAGAG AAAGGGGTAG GAAATGCGAT TTTATTATCA AATAAAATAA 1110       1120       1130       1140       1150
TTTTGAATAT TTTTTATTTA TATACGTATA TATAGACTAT TATTTACTTT
AAAACTTATA AAAAATAAAT ATATGCATAT ATATCTGATA ATAAATGAAA 1160       1170       1180       1190       1200
TAATAGATTA TTAAGATTTT TATTAAAAAA AAATTCGTCC CTCTTTTTAA
ATTATCTAAT AATTCTAAAA ATAATTTTTT TTTAAGCAGG GAGAAAAATT 1210       1220       1230       1240       1250
TGCCTTTTAT GCAGTTTTTT TTTCCCATTC GATATTTCTA TGTTCGGGTT
ACGGAAAATA CGTCAAAAAA AAAGGGTAAG CTATAAAGAT ACAAGCCCAA 1260       1270       1280       1290       1300
TCAGCGTATT TTAAGTTTAA TAACTCGAAA ATTCTGCGTT TCGAAAAAGC
AGTCGCATAA AATTCAAATT ATTGAGCTTT TAAGACGCAA AGCTTTTTCG TCGGTCGAC
AGCCAGCTG
  SalI
```

TABLE 3
pING323CVS Sequence

```
      10         20         30         40         50
GGATCCCGAC TCTTTTCTTC TAACCAAGGG GGTGGTTTAG TTTAGTAGAA
CCTAGGGCTG AGAAAAGAAG ATTGGTTCCC CCACCAAATC AAATCATCTT
BamHI 60         70         80         90        100
CCTCGTGAAA CTTACATTTA CATATATATA AACTTGCATA AATTGGTCAA
GGAGCACTTT GAATGTAAAT GTATATATAT TTGAACGTAT TTAACCAGTT 110        120        130        140        150
TAGCAGAAAT AGATATTTGG TCTTTTCTAA TTCGTAGTTT TTCAAGTTCT
ACGTTCTTTA TCTATAAACC AGAAAAGATT AAGCATCAAA AAGTTCAAGA 160        170        180        190        200
TAGATGCTTT CTTTTTCTCT TTTTTACAGA TCATCAAGGA AGTAATTATC
ATCTACGAAA GAAAAGAGA AAAAATGTCT AGTAGTTCCT TCATTAATAG

PGK Promoter◄──┼──►SUC2 signal sequence
     210        220        230        240        250
TACTTTTTAC AACAAATATA AAAACAAGAT CATGCTTTTG GAAGCTTTCC
ATGAAAAATG TTGTTTATAT TTTTGTTCTA GTACGAAAAC GTTCGAAAGG ◄──┼──►YT323
     260        270        280        290        300
TTTTCCTTTT GGCTGGTTTT GCAGCCAAAA TATCTGCCGC TACCTTCGAA
AAAAGGAAAA CCGACCAAAA CGTCGGTTTT ATAGACGGCG ATGGAAGCTT 310        320        330        340        350
ATCGTTAACA GATGTTCTTA CACTGTTTGG GCTGCTGCTT CCAAGGGTGA
TAGCAATTGT CTACAAGAAT GTGACAAACC CGACGACGAA GGTTCCCACT 360        370        380        390        400
CGCTGCTTTG GACGCCGGTG GTAGACAATT GAACTCTGGT GAATCCTGGA
GCGACGAAAC CTGCGGCCAC CATCTGTTAA CTTGAGACCA CTTAGGACCT
```

TABLE 3-continued
pING323CVS Sequence

```
           410          420          430          440          450
CCATCAACGT CGAACCAGGT ACCAAGGGTG GTAAGATCTG GCTAGAACC
GGTAGTTGCA GCTTGGTCCA TGGTTCCCAC CATTCTAGAC CCGATCTTGG
                                      BglII 460          470          480          490          500
GACTGTTACT TCGATGACTC TGGTTCCGGT ATCTGTAAGA CTGGTGACTG
CTGACAATGA AGCTACTGAG ACCAAGGCCA TAGACATTCT GACCACTGAC 510          520          530          540          550
TGGTGGTTTG TTGAGATGTA AGAGATTCGG TAGACCACCA ACCACTTTGG
ACCACCAAAC AACTCTACAT TCTCTAAGCC ATCTGGTGGT TGGTGAAACC 560          570          580          590          600
CTGAATTCTC TTTGAACCAA TACGGTGACG ACTACATCGA TATCTCCAAC
GACTTAAGAG AAACTTGGTT ATGCCACTGC TGATGTAGCT ATAGAGGTTG
                                Asp97

610          620          630          640          650
ATCAAGGGTT TCAACGTTCC AATGGACTTC TCTCCAACCA CTAGAGGTTG
TAGTTCCCAA AGTTGCAAGG TTACCTGAAG AGAGGTTGGT CATCTCCAAC 660          670          680          690          700
TAGAGGCGTC AGATGTGCTG CTGACATCGT TGGTCAATGT CCAGCTAAGC
ATCTCCGCAG TCTACACGAC GACTGTAGCA ACCAGTTACA GGTCGATTCG 710          720          730          740          750
TTAAGGCTCC AGGTGGTGGT TGTAACGACG CTTGTACCGT TTTCCAAACT
AATTCCGAGC TCCACCACCA ACATTGCTGC GAACATGGCA AAAGGTTTGA 760          770          780          790          800
TCCGAATACT GTTGTACCAC TGGTAAGTGT GGTCCAACCG AATACTCTAG
AGGCTTATGA CAACATGGTG ACCATTCACA CCAGGTTGGC TTATGAGATC 810          820          830          840          850
ATTCTTCAAG AGATTGTGTC CAGACGCTTT CTCCTACGTC TTGGACAAGC
TAAGAAGTTC TCTAACACAG GTCTGCGAAA GAGGATGCAG AACCTGTTCG 860          870          880          890          900
CAACTACCGT CACTTGTCCA GGTTCTTCCA ACTACAGAGT TACCTTCTGT
GTTGATGGCA GTGAACAGGT CCAAGAAGGT TGATGTCTCA ATGGAAGACA

YT323◄───|───►PGK terminator
           910          920          930          940          950
CCAACTGCCT AATGACTCGA GGGATCTCCC ATGTCTCTAC TGGTGGTGGT
GGTTGACGGA TTACTGAGCT CCCTAGAGGG TACAGAGATG ACCACCACCA
                       XhoI 960          970          980          990         1000
GCTTCTTTGG AATTATTGGA AGGTAAGGAA TTGCCAGGTG TTGCTTTCTT
CGAAGAAACC TTAATAACCT TCCATTCCTT AACGGTCCAC AACGAAAGAA 1010         1020         1030         1040         1050
ATCCGAAAAG AAATAAATTG AATTGAATTG AAATCGATAG ATCAATTTTT
TAGGCTTTTC TTTATTTAAC TTAAGCATAT ATATCTGATA TAGTTAAAAA 1060         1070         1080         1090         1100
TTCTTTTCTC TTTCCCCATC CTTTACGCTA AAATAATAGT TTATTTTATT
AAGAAAAGAG AAAGGGGTAG GAAATGCGAT TTTATTATCA AATAAAATAA 1110         1120         1130         1140         1150
TTTTGAATAT TTTTTATTTA TATACGTATA TATAGACTAT TATTTACTTT
AAAACTTATA AAAATAAAT ATATGCATAT ATATCTGATA ATAAATGAAA 1160         1170         1180         1190         1200
TAATAGATTA TTAAGATTTT TATTAAAAAA AAATTCGTCC CTCTTTTTAA
ATTATCTAAT AATTCTAAAA ATAATTTTTT TTTAAGCAGG GAGAAAAATT 1210         1220         1230         1240         1250
TGCCTTTTAT GCAGTTTTTT TTTCCCATTC GATATTTCTA TGTTCGGGTT
ACGGAAAATA CGTCAAAAAA AAAGGGTAAG CTATAAAGAT ACAAGCCCAA 1260         1270         1280         1290         1300
TCAGCGTATT TTAAGTTTAA TAACTCGAAA ATTCTGCGTT TCGAAAAAGC
AGTCGCATAA AATTCAAATT ATTGAGCTTT TAAGACGCAA AGCTTTTTCG
```

TABLE 3-continued pING323CVS Sequence

TCGGTCGAC
AGCCAGCTG
 SalI

EXAMPLE 4

Purification from Growth Media

In this example methods are described for purification of thaumatin produced by transformed cells and secreted into growth medium. According to methods for purification of thaumatin from cultures grown in shaker flasks (0.2 to 20 liters) or in small scale fermentors (10 to 75 liters), culture medium is clarified by continuous flow centrifugation (Westfalia SA-1) to pellet yeast cells.

The cell-free growth medium is then concentrated ten to twenty-fold using an Amicon DC-10L concentrator fitted with a 10,000 dalton molecular weight cutoff spiral cartridge and washed with 15 volumes of water. The concentrate is then centrifuged at 17,000×g for 20 minutes in order to clarify (with hollow fiber cartridges used for large volumes.) The supernatant is then filtered through a 0.45 μm pore size membrane in order to remove particulates and remaining cell debris. Sodium phosphate buffer is then added to a concentration of up to 10 mM in order to adjust the pH to between 7 and 8.

The clarified growth medium concentrate is then loaded onto a Zeta Chrom-60 SP disc (Western Analytical, sulfopropyl cation exchanger). The disk is washed with buffer, 10 mM sodium or potassium phosphate buffer pH 7-8, and the flow-through discarded after testing for the presence of thaumatin by radioimmunoassay. The thaumatin concentrated on the SP-resin is then eluted from the disc with 200 ml of a 250 mM NaCl solution in the buffer used previously. The dilute thaumatin solution is then concentrated by pressure ultrafiltration on an Amicon stirred cell fitted with a YM-5 membrane and washed twice with water to yield a substantially purified product (i.e., greater than 95%).

When thaumatin is purified from growth media from a larger scale fermentation (i.e., 400 to 600 liters) a modified purification procedure is followed. The fermentation medium is first subjected to an inactivation procedure comprising treatment with phosphoric acid to reach pH 4.0, addition of 0.4% sodium benzoate (w/v) and incubation at 30° C. for 30 minutes with no aeration. The cells were pelleted by centrifugation then killed with 5% bleach.

The cell-free growth medium is then concentrated ten to twenty fold using an Amicon DC-30P concentrator fitted with six 10,000 molecular weight cutoff spiral cartridges and washed with five volumes of water. The medium is then clarified within an Amicon hollow filter cartridge with a 0.1 μm cut off and washed with 15 liters of 250 mM NaCl in 10 mM sodium phosphate, pH 7-8. At this time the medium is concentrated using an Amicon DC-10L concentrator, centrifuged at 17,000×g, filtered through a 0.45 μm millipore membrane and buffered to pH 7 to 8 in the same manner as described for the smaller scale fermentations.

The clarified growth medium concentrate is then loaded onto a Zeta Chrom (Western Analytical) 100 cc SP capsule at a maximum flow rate of 20 ml per minute and washed with 10 mM sodium or potassium phosphate buffer pH 7-8. The concentrated protein is then eluted using one liter of 250 mM NaCl in the buffer. The eluate is monitored for protein elution with the Bio Rad Protein Assay. The protein positive fractions are then pooled and desalted/concentrated by ultrafiltration using an Amicon stirred cell fitted with a YM-5 membrane to yield a substantially purified product.

EXAMPLE 5

In this example, various improved yeast secretion signal sequences were constructed. Plasmid pKS48 was constructed for introducing sequence changes (primarily to encode positively charged amino acids) into the 5'-end of the SUC2 wild type yeast invertase signal sequence. Plasmid pSH4 which contains the 218 bp PGK promoter with SphI - SstI - XhoI linkers at the 3'-end was digested with XhoI, filled-in with T4 DNA polymerase and then digested with BamHI. The BamHI-blunt-end 218 bp PGK promoter fragment was ligated to HindIII digested, T4 polymerase blunt-ended, BamHI cut pKK108 to generate pKS48. Plasmid pKS48 contains the 218 bp PGK promoter, a partial invertase signal sequence and the partial thaumatin gene.

Digesting pKS48 with SphI and HindIII allows insertion of synthetic oligonucleotides to change the 5'-end of the invertase signal sequence. Five oligonucleotides were synthesized. The amino acid sequence changes they code for are shown in Table 4 below.

TABLE 4

| | |
|---|---|
| 1) 5'-AGCTTGCAATCTCATG-3' | Leu (1) ⟶ Arg |
| 2) 5'-AGCTTGTCTCAACATG-3' | Leu (2) ⟶ Arg |
| 3) 5'-AGCTTTCAACAACATG-3' | Gln (3) ⟶ Lys |
| 4) 5'-AGCTTGCTTCTTCTTCAACATG-3' | Leu (2) ⟶ Lys Lys Lys |
| 5) 5'-AGCTTGTCTCTTTCTCTTCAACATG-3' | Leu (2) ⟶ Lys Arg Lys Arg |

Each synthetic oligonucleotide was ligated to plasmid pKS48 that had been cut with SphI and HindIII. Upon transformation into *E. coli* strain MC1061, the single-stranded gaps were repaired in vivo (Huang, et al., Biochemistry, (1987), 26:8242–8246) to form plasmids pKS48-1 [Leu(1)→Arg], pKS48-2 [Leu(2)→Arg], pKS48-3 [Gln(3)→Lys], pKS55 [Leu(2)→LysLysLys), and pKS56 [Leu(2)→LysArgLysArg]. The BamHI-EcoRI fragments which contain the 218 bp PGK promoter-mutated signal sequence-partial thaumatin gene sequence were purified from all five plasmids individually. Also, an EcoRI-XhoI fragment which contains the 3'-half of a gene designated YT406 encoding [$Lys^{46}$, $Asp^{113}$] thaumatin I was purified from pING95CVS or pING438CVS (although the YT406 gene could have been obtained from other plasmids such as pKS6). The BamHI-EcoRI fragments from pKS48-1, pKS48-2 and pKS48-3 were ligated to the EcoRI-XhoI fragment from pING95CVS and BamHI-XhoI digested pING58 (a plasmid containing a PGK terminator sequence, the construction of which is described in co-owned and copending U.S. patent application Ser. No. 189,250 filed May 2, 1988) to form pING447, pING448 and pING449, respectively. The BamHI-EcoRI fragments from pKS55 and pKS56 were ligated to the EcoRI-XhoI fragment from pING438CVS and BamHI-XhoI digested pING58 to form plasmids pING454 and pING456, respectively.

To increase hydrophobicity in the center portion of the SUC2 signal sequence, a synthetic oligonucleotide (5'GCTTTCTTGATCTTGTTGATTTTGTTC-CAGGT AAGATCTCTGCCTGCA 3') was used to replace the small HindIII-PstI fragment of pKS46 by the in vivo gap-filling technique to generate pKS49. The thaumatin gene from pING174 was joined as an in-phase fusion to the new signal sequence of pKS49 by a two step cloning to form pKS54. The 218 bp PGK promoter-signal sequence-thaumatin gene was cloned into pING58 as a BamHI-XhoI fragment to generate pING451. In plasmid pING451, the following substitutions in the SUC2 secretion signal sequence were made: [$Phe^7$→Ile, $Ala^{10}$→Ile, $Gly^{11}$→Leu, $Ala^{13}$→Pro and $Ala^{14}$→Gly].

Combining the changes in pKS55 and pKS56 with those in pKS54 was done as follows. The small BamHI-HindIII fragments from pKS55 and pKS56 were ligated with the small HindIII-KpnI fragment from pKS54 into BamHI-KpnI cut pKS6 to form pKS57 and pKS58, respectively. The BamHI-XhoI fragments (about 920 bp, containing the promoter - signal - thaumatin fusions) from pKS57 and pKS58 were then cloned into BamHI and XhoI cut pING58 to form pING460 and pING462, respectively. These plasmids encoded secretion signal sequences with both positively charged amino acid residues at the amino end of the sequence and increased hydrophobicity in the center of the molecule.

Yeast strain BB33-lc [MATa, leu 2-3, 2-112, ura3-52] was transformed with plasmids pING156, pING447, pING448, pING449, pING451, pING454, pING456, pING460 and pING462. The Leu+ transformants were selected on SD-leu plates and single colonies picked into SD-leu broth and grown for 4 days. Samples were then taken for radioimmunoassay. The maximum yield of [$Lys^{46}$, $Asp^{113}$] thaumatin I production compared to the transformation lag time was recorded in Table 5 below.

TABLE 5

Effect of Modified Signal Sequences on Thaumatin Secretion

| Construct | Max. Yield (μg/ml) | Lag Time (days) |
|---|---|---|
| Wild Type Sequence, pING156<br>N—Met Leu Leu Gln Ala Phe Leu Phe Leu Leu Ala Gly Phe Ala Ala Lys Ser Ala—C<br>ATG CTT TTG CAA GCT TTC CTT TTC CTT TTG GCT GGT TTT GCA GCC AAA TCT GCC<br>                Hind III | 1.0 | 20–30 |
| pING447, Leu to Arg at 1<br>N—Met Arg Leu Gln Ala Phe Leu Phe Leu Leu Ala Gly Phe Ala Ala Lys Ile Ser Ala—C<br>ATG AGA CAA GCT TTC CTT TTC CTT TTG GCT GGT TTT GCA GCC AAA ATA TCT GCC | 1.8 | 10–14 |
| pING448, Leu to Arg at 2<br>N—Met Leu Arg Gln Ala Phe Leu Phe Leu Leu Ala Gly Phe Ala Ala Lys Ile Ser Ala—C<br>ATG TTG AGA CAA GCT TTC CTT TTC CTT TTG GCT GGT TTT GCA GCC AAA ATA TCT GCC | 0.3 | 10–14 |
| pING449, Gln to Lys at 3<br>N—Met Leu Leu Lys Ala Phe Leu Phe Leu Leu Ala Gly Phe Ala Ala Lys Ile Ser Ala—C<br>ATG TTG TTG AAA GCT TTC CTT TTC CTT TTG GCT GGT TTT GCA GCC AAA ATA TCT GCC | 0.4 | 10–14 |
| pING451, 5 amino acids changes<br>N—Met Leu Leu Gln Ala Phe Leu Ile Leu Leu Ile Leu Phe Leu Pro Gly Lys Ile Ser Ala—C<br>ATG CTT TTG CAA GCT TTC TTG ATC TTG TTG ATT TTG TTC CCA GGT AAG ATC TCT GCC | 0.4 | 10–14 |
| pING454<br>N—Met Leu Lys Lys Lys Gln Ala Phe Leu Phe Leu Leu Ala Gly Phe Ala Ala Lys Ile Ser Ala—C<br>ATG TTG AAG AAG AAG CAA GCT TTC CTT TTC CTT TTG GCT GGT TTT GCA GCC AAA ATA TCT GCC | 1.6 | 10–14 |
| pING456<br>N—Met Leu Arg Lys Arg Gln Ala Phe Leu Phe Leu Leu Ala Gly Phe Ala Ala Lys Ile Ser Ala—C<br>ATG TTG AGA AAG AGA CAA GCT TTC CTT TTC CTT TTG GCT GGT TTT GCA GCC AAA ATA TCT GCC | 1.0 | 4–5 |
| pING460<br>N—Met Leu Arg Lys Arg GlN Ala Phe Leu Ile Leu Leu Ile Leu Phe Pro Gly Lys Ile Ser Ala—C<br>ATG TTG AGA AAG AGA CAA GCT TTC TTG ATC TTG TTG ATT TTG TTC CCA GGT AAG ATC TCT GCC | 1.1 | 2–4 |
| pING462<br>N—Met Leu Lys Lys Lys Gln Ala Phe Leu Ile Leu Leu Ile Leu Phe Pro Gly Lys Ile Ser Ala—C<br>ATG TTG AAG AAG AAG CAA GCT TTC TTG ATC TTG TTG ATT TTG TTC CCA GGT AAG ATC TCT GCC | 1.3 | 2–4 |

EXAMPLE 6

In this example, PS16, a preferred yeast strain that secretes higher quantities of preferred thaumatin was isolated. Strain BB33-lc (MATa leu2-3,2-112 ura3-52) was transformed with pING156 (a high copy number expression plasmid encoding [Lys$^{46}$, Asp$^{113}$] thaumatin I and comprising a wild type secretion signal sequence) by selecting for Leu+ transformants. A small fraction of the transformants secreted 0.3–0.6 μg/ml of thaumatin. One of these higher secreting transformants was later found to be no longer haploid and was designated PS11. PS11 containing pING156 was mutagenized with N-methyl-N′-nitronitrosoguanidine, and colonies were screened for increased secretion.

Screening involved growing colonies on SD-leu plates, lifting the colonies from the master plates onto nitrocellulose filters, and placing the filters colony side up onto fresh SD-leu plates. After 6 to 24 hours of growth, the colonies were washed from the filters, and the filters were checked for thaumatin by protein immunoblotting (Western procedure). Higher secreting colonies were picked from the master plate and rechecked by Western and RIA procedures. This approach was repeated by serially isolating higher secreting colonies to give the genealogy PS11[pING156]→PS6[pING156]→PS10-[pING156]→PS14[pING156]. PS14 was cured of the plasmid by growing on non-selective medium (YPD) and retransformed with pING460. Mutagenesis of PS14[pING460] yielded PS16[pING460]. Yeast strain PS16 is on deposit under contract with the American Type Culture Collection, 12301 Parklawn Drive, Rockville, Maryland 20852-1776 as A.T.C.C. Deposit No. 20909. The thaumatin secretion of each mutant in the series is shown in Table 6 below.

TABLE 6

[Lys$^{46}$, Asp$^{113}$] THAUMATIN I
SECRETION BY MUTANTS CONTAINING
VECTORS WITH DIFFERENT SIGNAL SEQUENCES

| | (μg/ml) assayed by RIA | | | | |
|---|---|---|---|---|---|
| | pING 462 | pING 460 | pING 456 | pING 156 | pING 94 |
| BB33-1C | 2.9 | >3.8 | 0.3 | — | 0.3 |
| PS11 | 5.0 | 5.4 | 1.4 | 0.6 | — |
| PS4 | — | — | — | 1.6 | 1.2 |
| PS5 | — | — | — | 2.0 | 0.9 |
| PS6 | >7.7 | 3.9 | — | 4.0 | 0.4 |
| PS10 | 6.8 | 7.7 | — | 5.0 | — |
| PS16 | — | 10.0 | — | — | — |

Construction of pING816A

Genomic DNA from *Kluyveromyces lactis* strain KG51-5A (ATCC #48792) was partially digested with the restriction enzyme Sau3A. Fragments 10–12 Kb in size were fractionated and collected on sucrose gradient. This DNA was ligated into pING1001RKnB that had been cut with BamHI (BamHI ends are compatible with Sau3A ends) to form a yeast genomic plasmid library. pING1001RKnB is a *S. cerevisiae* - *E. coli* shuttle vector containing the Tn903 aminoglycoside phosphotransferase gene linked to the *S. cerevisiae* 3-phosphoglycerate kinase (PGK) promoter. This allows transformation of the library into *S. cerevisiae* by selecting for resistance to the aminoglycoside G418. Plasmid pING1001RKnB is not critical to this procedure and may be replaced by other plasmids that have one or more markers complementing the host deficiency.

When the library was transformed into the yeast strain BB33-lc (MATa leu2-3, 2-112, ura3-52), a Ura+ transformant was isolated. Plasmid DNA was isolated from this transformant, transformed into *E. coli*, and harvested in a plasmid preparation. Although the BamHI site of pING1001RKnB is often destroyed when ligated with Sau3A ends (as it was in this case), it is flanked by two EcoRI sites (the only EcoRI sites in pING1001RKnB), which allows the DNA conferring Ura+ to BB33-lc to be removed as a 2.8 kb EcoRI fragment.

This 2.8 kb EcoRI fragment was blunt-ended by T4 DNA polymerase and ligated to the AatII cut, T4 DNA polymerase blunt-ended pING460 ([Lys$^{46}$, Asp$^{113}$] thaumatin I) described previously. Plasmids with either orientation of the *K. lactis* URA3 fragment were isolated as determined by the placement of an XhoI site at one end of the fragment with respect to the PstI site of the Amp$^R$ gene in the bacterial sequences of pING460. pING816A has the XhoI site about 1 kb from the PstI site, whereas pING816B has the XhoI site about 3 kb from the PstI site.

Plasmid pING816A transformants of yeast strain PS16 (a mutagenized derivative of BB33-lc), selected for Ura+, showed up in 3–4 days. They secreted about 10 μg/ml of thaumatin under Ura+ selection in liquid media. This level of thaumatin secretion was reproducible and appeared to be fairly stable. Selection for a Leu+ or a Leu+Ura+ phenotype with pING816A yielded lower levels of thaumatin secretion (2–3 μg/ml). About 37% of the cells were still Ura+ after about 20 generations in non-selective YPD medium.

EXAMPLE 7

In this example, thaumatin proteins produced from cells transformed with plasmids pING152T and pING323T {yeast thaumatin 152 (YT152) [Lys$^{46}$, Asp$^{113}$, Asp$^{137}$] thaumatin I and yeast thaumatin 323 (YT323) [Lys$^{46}$, Asp$^{97}$, Asp$^{113}$] thaumatin I, respectively} were tested by a taste panel and compared with plant derived thaumatin. Plant thaumatin is intensely sweet, but has a delayed onset followed by a rapid rise in sweetness intensity, a long lasting sweetness and a lingering aftertaste which has been described as "licorice-like." Higginbotham, et al., Flavor Potentiating Properties of Talin Sweetener (Thaumatin). The Quality of Foods and Beverages, Academic Press, New York, 91–111 (1981).

Fifteen potential subjects were screened for their ability to discriminate the basic tastes of sweet, sour, salty and bitter (2% sucrose, 0.07% citric acid, 0.2% sodium chloride,; 0.07% caffeine). Thirteen subjects (10 female and 3 male) successfully completed the screening program.

Following screening, the subjects participated in five, thirty minute sessions of training in descriptive analysis. The training included both round table discussion and testing in the partitioned sensory booths on samples selected to include sensory attributes and intensities representative of the sweeteners to be evaluated.

Training was completed once the subjects developed a descriptive sensory language with definitions, a scoresheet to measure the intensity of each characteristic, a standard procedure for examining and evaluating the products and demonstrated an ability to evaluate products using a scoresheet relating to eighteen flavor and aftertaste characteristics. (See Table 7 below.)

TABLE 7
Flavor and Aftertaste Characteristics of Thaumatin Proteins

WHILE IN MOUTH

| | |
|---|---|
| Initial Blandness: | The bland non-sweet taste right after the sample is put in the mouth. |
| Sweet: | The intensity of cane sugar type sweetness. |
| Bitter: | The taste stimulated by caffeine. |
| Salt: | The taste stimulated by table salt (sodium chloride). |
| Sour: | The taste stimulated by citric acid. |
| Caramelized Lactose: | The odor sensation on the back of the throat or nose similar to the odor of caramelized lactose or Eagle brand sweetened condensed milk. |
| Menthol Cool: | The cooling sensation in the mouth or nose produced by menthol or mint. |
| Licorice: | The taste stimulated by black licorice. |
| Medicinal: | The odor on the back of the throat or nose similar to cough syrup. |
| Mouth Coating: | Degree of coating perceived in the mouth after expectoration. |

AFTERTASTE:

| | |
|---|---|
| | The sensations following expectoration. |
| Sweet: | The residual sweetness after expectoration. |
| Licorice: | The residual licorice taste after expectoration. |
| Bitter: | The residual bitter taste after expectoration. |
| Sour: | The residual sour taste after expectoration. |
| Medicinal | The residual medicinal odor after expectoration. |
| Caramelized Lactose: | The residual caramelized lactose odor after expectoration. |
| Metallic: | The aftertaste similar to the taste of syrup of canned pineapple. |
| Mouth Watery: | The degree of salivation after expectoration. |
| Lingering: | The duration of sensation remain in the mouth after expectoration. |
| Intensified with Water: | The residual sensations reactivated with water. |

Test samples were prepared in 1 liter isosweet (10% sucrose equivalent) masterbatches and held at 38° F. for from one to three days for testing.

TABLE 8

| Product | Concentration | RIA Activity |
|---|---|---|
| Plant thaumatin | 0.01 g/250 ml | 49 μg/ml |
| YT152 | Calc. @ 95 μg/ml | 90 μg/ml |
| YT323 | Calc. @ 96 μg/ml | 145 μg/ml |

All testing was conducted in sensory booths which are designed to provide a controlled testing environment. Samples (10 mls) were served in 1 oz. odorless plastic cups. Each subject evaluated one sample at a time, and was provided with a 3 minute rest interval between samples. The subjects were asked to expectorate the samples, and to rinse with purified water and unsalted crackers between samples. All testing was done between 10:00 and 11:30 a.m. Samples were served to each subject coded only with three-digit random numbers. The numbers were different for each subject and each sample on each test.

Samples were served in a balanced block design, balanced for serving order, subject and day over the entire study. Each sample was evaluated by each of the thirteen subjects, once a day for three days, yielding approximately 39 observations per product on each of the eighteen attributes. The data were analyzed with a one-way analysis of variance to evaluate individual subject performance on each attribute, a two-way analysis of variance to evaluate overall panel performance on each attribute, and a Duncan Multiple Range Test to identify statistically significant differences between sample means.

Testing was also conducted with respect to the intensity of sweetness over time of the thaumatin proteins. Potential subjects were recruited and screened for their ability to detect sweetness in five suprathreshold concentrations of sucrose and plant thaumatin. Those who passed this initial screening were then tested for their ability to rank various concentrations of sucrose solutions in order from lowest to highest (5, 7.5, 10, 12.5 and 15% in water) according to the procedure of Swartz, et al., Food Technology, Vol. 31, 51–67 (1977). The thirteen to fifteen most accurate and reliable judges were selected to participate in the time-intensity studies.

Three practice sessions were conducted to give subjects basic instructions on the techniques of tasting and the method of operating the strip-chart recorder as described by Larson-Powers and Pangborn, J. Food Science, 43(1), 41–46 (1978). The subjects were then ready to being the time-intensity studies.

The sweetener concentrations were approximately equisweet with 10% (w/v) sucrose solution. These concentrations were derived at through the completion of isosweetness studies which were conducted to insure reliable time-intensity data. Subjects were given randomly numbered (3-digit) 10 ml samples of each sweetener, in a sequential monadic balanced order. The subjects were instructed to take the entire sample into their mouth, start the moving chart recorder with a foot pedal, and "mark along the line that best reflects the relative sweetness intensity of the sample." A line was marked on the paper at which point the subjects were instructed to expectorate the sample (ten seconds) and continue scoring sweetness intensity until all sweetness was gone. The subjects cleansed their mouth using water, unsalted crackers, and a few minutes time in between sample evaluations. This procedure was repeated for each sweetener being tested. Each study was replicated three times to help ensure consistency, increase statistical validity, and provide a high quality, sufficiently large data base on which to arrive at reliable conclusions.

The following four sensory characteristics from each individual recording were measured:
1. Intensity at Expectoration: The numerical intensity value, on a 100 unit scale at 10 seconds.
2. Maximum Intensity: The highest sweetness intensity value scored, on a 100 unit scale.
3. Time to Maximum: The number of seconds elapsed from time zero until the time it reaches maximum sweetness.
4. Total Duration: The number of seconds from time zero until all sweetness is gone and recording is stopped.

These data were analyzed with a one-way analysis of variance to evaluate individual panelist performance, a two-way analysis of variance to evaluate overall panel performance on each measurement, and a Duncan Multiple Range test to identify statistically significant differences between the sweeteners. All statistical analysis were performed at the 95% level of confidence.

Mean values were also calculated for each 2.5 second interval along the charts generated by each judge for each sweetener.

Figure 2:
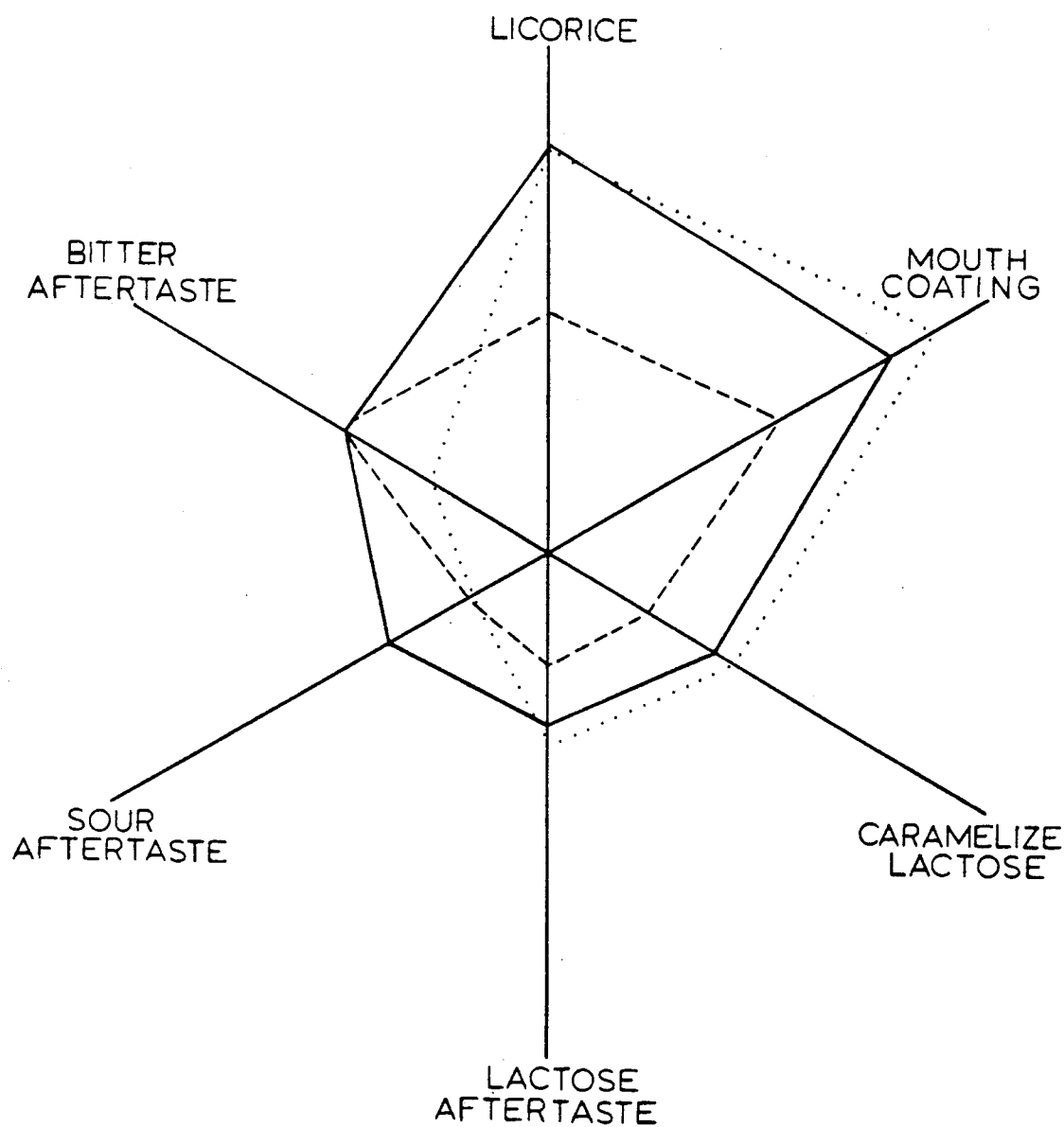
FIG. 2 is a depiction of the relative taste qualities of [Lys$^{46}$, Asp$^{97}$, Asp$^{113}$] and [Lys$^{46}$, Asp$^{113}$, Asp$^{137}$] thaumatin I polypeptides and plant derived thaumatin.

The testing obtained the results that YT152 and YT323 were not significantly different from plant produced thaumatin with respect to salty, sour, menthol cool, medicinal, medicinal aftertaste and menthol aftertaste. There were significant differences, however, on eleven of the eighteen attributes measured. Both YT152 at 90 μg/ml and YT323 at 145 μg/ml were equally sweet with plant thaumatin at 49 μg/ml. YT323 was most similar to thaumatin, but left a less sour and less bitter aftertaste. YT152 was quite different from thaumatin. YT152 had less licorice flavor and aftertaste, a less sour and less sweet aftertaste, was less mouth watering, had less of a mouth coating and had less overall lingering sweetness (FIGS. 1 and 2, Tables 7–9).

In separate studies, YT152 at 104 μg/ml and YT323 at 70 μg/ml were equally sweet with 49 μg/ml plant thaumatin, took less time to reach maximum sweetness intensity and had less lingering sweetness than plant thaumatin (Table 12).

These data clearly indicate that the latent sweetness onset and the lingering aftertaste of plant thaumatin has been significantly reduced for both YT152 and YT323. YT152 also has a significantly reduced "licorice-like" flavor and aftertaste which may broaden its potential applications.

TABLE 9

| Lingering | | Sweet | |
|---|---|---|---|
| Thaumatin | 29.77[a] | YT323 | 32.31[a] |
| YT323 | 28.36[a] | Thaumatin | 28.44[ab] |
| YT152 | 17.33 | YT152 | 25.17[b] |
| Sweet Aftertaste | | Mouth Watering | |
| YT323 | 22.51[a] | Thaumatin | 17.41[a] |
| Thaumatin | 21.64[a] | YT323 | 16.85[a] |
| YT152 | 15.85 | YT152 | 10.28 |
| Licorice Aftertaste | | | |
| Thaumatin | 22.82[a] | | |
| YT323 | 21.56[a] | | |

TABLE 9-continued

| YT152 | 13.69 |
|---|---|

[a]Means are not significantly different at the 0.5 level of probability.
[b]Means are not significantly different at the 0.5 level of probability.

TABLE 10

| Licorice | | Mouth Coating | |
|---|---|---|---|
| Thaumatin | 16.26[a] | YT323 | 17.72[a] |
| YT323 | 15.95[a] | Thaumatin | 15.72[a] |
| TY152 | 9.58 | YT152 | 10.59 |
| Caramelize Lactose | | Lactose Aftertaste | |
| YT323 | 8.56[a] | YT323 | 7.67[a] |
| Thaumatin | 7.67[ab] | Thaumatin | 6.85[ab] |
| YT152 | 4.58[b] | YT152 | 4.46[b] |
| Sour Aftertaste | | Bitter Aftertaste | |
| Thaumatin | 7.39 | YT152 | 9.69[a] |
| YT152 | 3.74[a] | Thaumatin | 9.46[a] |
| YT323 | 3.51[a] | YT323 | 5.49 |

[a]Means are not significantly different at the 0.5 level of probability.
[b]Means are not significantly different at the 0.5 level of probability.

TABLE 11

Summary of Significant Differences[1]

| (90 μg/ml) YT152 Has/Is: | (145 μg/ml) YT323 Has/Is: |
|---|---|
| Equal Sweetness | Equal Sweetness |
| Less Lingering Taste | Less Sour Aftertaste |
| Less Sweet Aftertaste | Less Bitter Aftertaste |
| Less Mouth Watering | |
| Less Licorice Flavor | |
| Less Licorice Aftertaste | |
| Less Mouth Coating | |
| Less Sour Aftertaste | |

[1]All attributes listed were significantly different at p < 0.05.

TABLE 12

| Sweetener Characteristics - Time Intensity | | | | | |
|---|---|---|---|---|---|
| YT152 (104 μg/ml) (N = 13, Rep = 3) | | Standard Error | YT323 (70 μg/ml) (N = 15, Rep = 3) | | Standard Error |
| A. Intensity at Expectoration | | | A. Intensity at Expectoration | | |
| YT152 | 64.31[a] | 3.63 | Thaumatin | 67.6[a] | 3.86 |
| Thaumatin | 63.18[a] | 3.98 | YT323 | 64.9[a] | 4.03 |
| B. Maximum Sweetness Intensity | | | B. Maximum Sweetness Intensity | | |
| Thaumatin | 73.23[a] | 3.85 | Thaumatin | 72.8[a] | 3.92 |
| YT152 | 70.72[a] | 3.82 | YT323 | 70.5[a] | 4.09 |
| C. Time to Maximum | | | C. Time to Maximum | | |
| Thaumatin | 14.25 | 1.15 | Thaumatin | 11.8[b] | 0.65 |
| YT152 | 12.54 | 0.83 | YT323 | 10.6[b] | 0.56 |
| D. Total Duration | | | D. Total Duration | | |
| Thaumatin | 40.72 | 4.01 | Thaumatin | 36.5 | 2.56 |
| YT152 | 33.10 | 2.71 | YT323 | 31.4 | 2.36 |

[a]Means are not significantly different at the 0.5 level of probability.
[b]Means represent interpreted trends based on ranks and individual respondent data.

EXAMPLE 8

In this example, KHK1, a preferred yeast strain derived from PS16 was isolated. A PS16 [pING816A] transformant was streaked onto SD-ura agar for single colony isolation. Sixteen colonies were tested for thaumatin secretion by growth for four days in 3 mls of liquid SD⁻ura. One of these, called BB2, which secreted 12.9 μg/ml of thaumatin, was sub-cloned by re-streaking onto SD⁻ura agar. Four colonies were picked for growth in SD⁻liquid. One of these, KHK1 (originally BB2a) secreted 14–17 μg/ml. Yeast strain KHK1 is on deposit under contract with the American Type Culture Collection, 12301 Parklawn Drive, Rockville, Maryland 20852-1776 as A.T.C.C. Deposit No. 20954.

Because of the XhoI site in the EcoRI fragment containing the uraA gene, the pING816A plasmid background was inconvenient for routine cloning of BamHI-XhoI fragments in front of the PGK terminator. Therefore, a similar plasmid background was constructed with this XhoI site destroyed. pING816A was cleaved with BamHI and XbaI, blunt-ended with T4 DNA polymerase, and ligated. This removed approximately 2900 bp, destroying the XbaI site and recreating the BamHI site. This intermediate plasmid, pKK135, was then cleaved with XhoI, blunt-ended with T4 DNA polymerase, and religated, thus destroying the XhoI site but creating a PvuI site. This second intermediate, pKK136, was cut with BamHI and HpaI and ligated with the approximately 2150 bp BamHI-HpaI fragment of pING58. The resulting plasmid, pING827, contains the betalactamase gene for ampicillin selection and the colEI replicon for replication in E. coli; the uraA gene from K. lactis and the leu2-d marker which can provide URA3 and partial LEU2 functions to S. cerevisiae as selectable markers; the origin of replication and STB (REP3) functions of the endogenous 2-micron plasmid for replication of pING827 in S. cerevisiae; and the PGK terminator behind a unique XhoI site.

Plasmid pING827 is suitable for cloning BamHI-XhoI fragments containing a promoter (in this case the PGK promoter) and a functional gene following the promoter (in this case a thaumatin gene having a secretion signal) in front of the PGK terminator. Plasmid pING834 was constructed by replacing the approximately 190 bp BamHI-XhoI fragment of pING827 with the approximately 1280 bp BamHI-XhoI fragment from pING460. This effectively created a version of pING8-16A with the XhoI site in uraA destroyed. Like pING8-16A, pING834 has the [Lys$^{46}$, Asp$^{113}$] thaumatin I coding sequence.

A related plasmid, pING835, containing the [Lys$^{46}$, Asp$^{113}$, Asp$^{137}$] thaumatin I coding sequence can be constructed by ligation of three restriction fragments: The large BamHI-XhoI fragment of pING827; an approximately 540 bp BamHI-EcoRI fragment from pING460 containing the PGK promoter, the signal sequence, and the 5' portion of the [Lys$^{46}$, Asp$^{113}$] thaumatin I coding sequence; and an approximately 267 bp EcoRI-XhoI fragment containing the 3' portion of the [Lys$^{46}$, Asp$^{113}$, Asp$^{137}$] thaumatin I coding sequence. This EcoRI-XhoI fragment can be supplied from pING152CVS, but was, in fact, supplied from another plasmid, pING152KRS.

KHK1 [pING816A] was grown in small-scale fermenters where the level of secreted thaumatin present in the clarified culture media consistently exceeded 100 mg/liter. Specifically, seed cultures of PS-16 or KHK1 with plasmid pING816A, pING834 or pING835 were grown at 30° C. in SD-ura with six times, i.e., 0.18 g/L, the normal amount of leucine. 5-50 mls of seed culture of OD$_{600}$>2 were inoculated aseptically into about one liter of a batch medium based on Fieschko, et al., Biotech. & Bioeng., Vol. XXIX, pp. 1113-1121, John Wiley & Sons (1987), produced by combining 90 parts by volume of a solution comprising 23.0 g/L casaminoacids, 4.0 g/L ammonium sulfate and 13.0 g/L potassium phosphate (monobasic) with 10 parts of separately autoclaved additions comprising Part 1 (2.0 g/L glucose, 1.0 g/L magnesium sulfate and 0.1 g/L inositol) and Part 2 (3.0 ml/L vitamin solution, 3.0 ml/L trace metals solution and 3.0 ml/L 1% thiamine solution). Although selection is maintained during growth of the seed, the exact method of seed growth is not considered crucial. The fermenter culture was grown at 30° C., while maintaining the pH at 5.5 with 40% ammonium hydroxide addition, and maintaining the dissolved oxygen with forced air and oxygen at greater than 35%. When the OD$_{600}$ reached approximately 1 in the fermenter, feed medium based on Fieschko, et al. and comprising 530 ml of Part 1 (100 g/L casamino acids, 3.0 g/L potassium phosphate (monobasic), 5.0 g/L ammonium sulfate, 0.5 ml/L polypropylene glycol and 465.0 ml/L RO (reverse osmosis)-H$_2$O) and 455 ml of Part 2 (500.0 g/L glucose, 15.0 ml/L 1M magnesium sulfate, 0.1 g/L inositol and 120 ml/L RO-H$_2$O) to which had been added after heating to dissolve the glucose 7.0 ml vitamin solution, 7.0 ml of trace metals solution and 2.0 mls 1% thiamine solution. The feed solution was added starting at a rate of about 1 ml/hour. The feed was stepped up proportionally to the OD$_{600}$ (determined by withdrawing and measuring samples from the fermenter) but, more importantly, the ethanol concentration (from yeast metabolism) was maintained at less than 0.1 g/L. The fermentation was continued for 2 to 8 hours after the feed had run out. The typical final OD$_{600}$ was greater than 200 but less than 250.

The values for thaumatin secreted were determined by an ELISA using thaumatin specific monoclonal and polyclonal antibodies. The amounts of thaumatin secreted into fermentation media were measured by at least one of two additional methods: (1) band intensity of desalted media run on SDS polyacrylamide gels stained with Coomassie blue; and (2) protein peak areas of media samples eluted using cation exchange chromatography (either HPLC or FPLC). For HPLC, a ten minute gradient of 0-500 mM NaCl in 10 mM Na-PO$_4$, pH 6.9, over a BioRad HRLC MA7C column (carboxymethyl groups) was used. For FPLC, the same gradient in 20 mM MES [2-N-Morpholino) Ethanesulfonic Acid], pH 6.0, over a Rainin Hydropore-SCX column was used. According to this method of cation exchange chromatography, thaumatin elutes as a single peak while other media proteins fail to bind to the column in this chromatography scheme.

Numerous modifications and variations in practice of the invention are expected to occur to those skilled in the art upon consideration of the foregoing descriptions of preferred embodiments thereof. In particular, it is expected that in light of applicants' discovery of the importance of the 97th and 137th amino acid residues to the taste characteristics of the thaumatin I molecule, that additional thaumatin I molecules having improved taste characteristics can be produced by substitution of amino acids other than aspartic acid for lysine at positions 97 and 137.

What is claimed is:

1. A purified and isolated DNA sequence capable of directing the synthesis in a selected host microorganism of [Lys$^{46}$, Asp$^{97}$, Asp$^{113}$] Thaumatin I.

2. A purified and isolated DNA sequence according to claim 1 comprising the following sequence of nucleotide bases in the coding strand thereof:

```
                    1                              10
          Ala Thr Phe Glu Ile Val Asn Arg Gly Ser Tyr Thr Val
       5'-GCT ACC TTC GAA ATC GTT AAC AGA TGT TCT TAC ACT GTT

20
          Trp Ala Ala Ala Ser Lys Gly Asp Ala Ala Leu Asp Ala Gly
          TGG GCT GCT GCT TCC AAG GGT GAC GCT GCT TTG GAC GCC GGT 30                                       40
          Gly Arg Gln Leu Asn Ser Gly Glu Ser Trp Thr Ile Asn Val
          GGT AGA CAA TTG AAC TCT GGT GAA TCC TGG ACC ATC AAC GTC

50
          Glu Pro Lys Thr Lys Gly Gly Lys Ile Trp Ala Arg Thr Asp
          GAA CCA GGT ACC AAG GGT GGT AAG ATC TGG GCT AGA ACC GAC

60
          Cys Tyr Phe Asp Asp Ser Gly Ser Gly Ile Cys Lys Thr Gly
          TGT TAC TTC GAT GAC TCT GGT TCC GGT ATC TGT AAG ACT GGT 70                                  80
          Asp Cys Gly Gly Leu Leu Arg Cys Lys Arg Phe Gly Arg Pro
          GAC TCT GGT GGT TTG TTG AGA TGT AAG AGA TTC GGT AGA CCA

90
          Pro Thr Thr Leu Ala Glu Phe Ser Leu Asn Gln Tyr Gly Asp
          CCA ACC ACT TTG GCT GAA TTC TCT TTG AAC CAA TAC GGT GAC 100                           100
          Asp Tyr Ile Asp Ile Ser Asn Ile Lys Gly Phe Asn Val Pro
          GAC TAC ATC GAT ATC TCC AAC ATC AAG GGT TTC AAC GTT CCA

120
          Met Asp Phe Ser Pro Thr Thr Arg Gly Cys Arg Gly Val Arg
          ATG GAC TTC TCT CCA ACC ACT AGA GGT TGT AGA GGC GTC AGA

130
          Cys Ala Ala Asp Ile Val Gly Gln Cys Pro Ala Lys Leu Lys
          TGT GCT GCT GAC ATC GTT GGT CAA TGT CCA GCT AAG CTT AAG 140                              150
          Ala Pro Gly Gly Gly Cys Asn Asp Ala Cys Thr Val Phe Gln
          GCT CCA GGT GGT GGT TGT AAC GAC GCT TGT ACC GTT TTC CAA

160
          Thr Ser Glu Tyr Cys Cys Thr Thr Gly Lys Cys Gly Pro Thr
          ACT TCC GAA TAC TGT TGT ACC ACT GGT AAG TGT GGT CCA ACC 170                           180
          Glu Tyr Ser Arg Phe Phe Lys Arg Leu Cys Pro Asp Ala Phe
          GAA TAC TCT AGA TTC TTC AAG AGA TTG TGT CCA GAC GCT TTC

190
          Ser Tyr Val Leu Asp Lys Pro Thr Thr Val Thr Cys Pro Gly
          TCC TAC GTC TTG GAC AAG CCA ACT ACC GTC ACT TGT CCA GGT

200
          Ser Ser Asn Tyr Arg Val Thr Phe Cys Pro Thr Ala
          TCT TCC AAC TAC AGA GTT ACC TTC TGT CCA ACT GCC-3'.
```

3. A purified and isolated DNA sequence according to claim 1 wherein the base sequence includes one or more codons selected from among alternative codons specifying the same amino acid on the basis of preferential expression characteristics of the codon in *E. coli.*

4. A purified and isolated DNA sequence according to claim 1 wherein the base sequence includes one or more codons selected from among alternative codons specifying the same amino acid on the basis of preferential expression characteristics of the codon in *Saccharomyces cerevisiae.*

5. A purified and isolated DNA sequence capable of directing the synthesis in a selected host microorganism of [Lys[46], Asp[113], Asp[137]] Thaumatin I.

6. A purified and isolated DNA sequence according to claim 5 comprising the following sequence of nucleotide bases in the coding strand thereof:

```
                    1                              10
          Ala Thr Phe Glu Ile Val Asn Arg Cys Ser Tyr Thr Val
       5'-GCT ACC TTC GAA ATC GTT AAC AGA TGT TCT TAC ACT GTT

20
          Trp Ala Ala Ala Ser Lys Gly Asp Ala Ala Leu Asp Ala Gly
          TGG GCT GCT GCT TCC AAG GGT GAC GCT GCT TTG GAC GCC GGT
```

```
                      30                                    40
Gly Arg Gln Leu Asn Ser Gly Glu Ser Trp Thr Ile Asn Val
GGT AGA CAA TTG AAC TCT GGT GAA TCC TGG ACC ATC AAC GTC

50
Glu Pro Gly Thr Lys Gly Gly Lys Ile Trp Ala Arg Thr Asp
GAA CCA GGT ACC AAG GGT GGT AAG ATC TGG GCT AGA ACC GAC

60
Cys Tyr Phe Asp Asp Ser Gly Ser Gly Ile Cys Lys Thr Gly
TGT TAC TTC GAT GAC TCT GGT TCC GGT ATC TGT AAG ACT GGT 70                                            80
Asp Cys Gly Gly Leu Leu Arg Cys Lys Arg Phe Gly Arg Pro
GAC TGT GGT GGT TTG TTG AGA TGT AAG AGA TTC GGT AGA CCA

90
Pro Thr Thr Leu Ala Glu Phe Ser Leu Asn Gln Tyr Gly Lys
CCA ACC ACT TTG GCT GAA TTC TCT TTG AAC CAA TAC GGT AAG 100                                       100
Asp Tyr Ile Asp Ile Ser Asn Ile Lys Gly Phe Asn Val Pro
GAC TAC ATC GAT ATC TCC AAC ATC AAG GGT TTC AAC GTT CCA

120
Met Asp Phe Ser Pro Thr Thr Arg Gly Cys Arg Gly Val Arg
ATG GAC TTC TCT CCA ACC ACT AGA GGT TGT AGA GGC GTC AGA

130
Cys Ala Ala Asp Ile Val Gly Gln Cys Pro Ala Asp Leu Lys
TGT GCT GCT GAC ATC GTT GGT CAA TGT CCA GCT GAC CTT AAG 140                                  150
Ala Pro Gly Gly Gly Cys Asn Asp Ala Cys Thr Val Phe Gln
GCT CCA GGT GGT GGT TGT AAC GAC GCT TGT ACC GTT TTC CAA

160
Thr Ser Glu Tyr Cys Cys Thr Thr Gly Lys Cys Gly Pro Thr
ACT TCC GAA TAC TGT TGT ACC ACT GGT AGG TGT GGT CCA ACC 170                                       180
Glu Tyr Ser Arg Phe Phe Lys Arg Leu Cys Pro Asp Ala Phe
GAA TAC TCT AGA TTC TTC AAG AGA TTG TGT CCA GAC GCT TTC

190
Ser Tyr Val Leu Asp Lys Pro Thr Thr Val Thr Cys Pro Gly
TCC TAC GTC TTG GAC AAG CCA ACT ACC GTC ACT TGT CCA GGT

200
Ser Ser Asn Tyr Arg Val Thr Phe Cys Pro Thr Ala
TCT TCC AAC TAC AGA GTT ACC TTC TGT CCA ACT GCC-3'.
```

7. A purified and isolated DNA sequence according to claim 5 wherein the base sequence includes one or more codons selected from among alternative codons specifying the same amino acid on the basis of preferential expression characteristics of the codon in E. coli.

8. A purified and isolated DNA sequence according to claim 5 wherein the base sequence includes one or more codons selected from among alternative codons specifying the same amino acid on the basis of preferential expression characteristics of the codon in Saccharomyces cerevisiae.

9. A biologically functional DNA microorganism transformation vector including a gene capable of directing the synthesis in a selected host microorganism of [Lys$^{46}$, Asp$^{97}$, Asp$^{113}$] Thaumatin I.

10. A biologically functional DNA microorganism transformation vector including a gene capable of directing the synthesis in a selected host microorganism of [Lys$^{46}$, Asp$^{113}$, Asp$^{137}$] Thaumatin I.

11. A microorganism transformed with a vector including a gene capable of directing the synthesis of [Lys$^{46}$, Asp$^{97}$, Asp$^{113}$] Thaumatin I.

12. A microorganism transformed with a vector including a gene capable of directing the synthesis of [Lys$^{46}$, Asp$^{113}$, Asp$^{137}$] Thaumatin I.

13. The microorganisms of claims 11 or 12 which are E. coli microorganisms.

14. The microorganisms of claims 11 or 12 which are Saccharomyces cerevisiae microorganisms.

15. Yeast strain deposited as A.T.C.C. No. 20909.

16. Yeast strain deposited as A.T.C.C. No. 20954.

* * * * *

UNITED STATES PATENT AND TRADEMARK OFFICE
CERTIFICATE OF CORRECTION

PATENT NO. : 5,221,624

DATED : June 22, 1993

INVENTOR(S) : Blair et al.

It is certified that error appears in the above-identified patent and that said Letters Patent is hereby corrected as shown below:

Column 7, Table 2, "     110                    --        110
          TAGCAGAAAT" should be    TGCAAGAAAT--.

Column 9, Table 3, "     110                    --        110
          TAGCAGAAAT" should be    TGCAAGAAAT--.

Column 9, Table 3, "     250                    --        250
          GAAGCTTTCC" should be    CAAGCTTTCC--.

Column 11, Table 3, "    650                    --        650
           CTAGAGGTTG                         CTAGAGGTTG
           CATCTCCAAC" should be    GATCTCCAAC--.

Column 17, Table 5, in sequencing for pING156, between
"Lys  and "Ser   insert  --Ile
 AAA"     TCT"           ATA--.

Column 18, Table 5, in sequencing for pING460,
"Gln   should be  --Gln
 CAA"             CAA--.

Column 27, claim 2, position 44, "Lys" should be --Gly--.

Column 27, claim 2, position 71, "TCT" should be --TGT--.

Column 27, claim 2, position "100" (second occurrence),
should be position --110--.

UNITED STATES PATENT AND TRADEMARK OFFICE
CERTIFICATE OF CORRECTION

PATENT NO.  :  5,221,624

DATED       :  June 22, 1993

INVENTOR(S) :  Blair et al.

It is certified that error appears in the above-identified patent and that said Letters Patent is hereby corrected as shown below:

Column 27, claim 2, position 163, "AGG" should be
--AAG--.

Column 29, claim 6, position 71, "TCT" should be --TGT--.

Column 29, claim 6, position 163, "AGG" should be
--AAG--.

Signed and Sealed this

Twentieth Day of September, 1994

Attest:

BRUCE LEHMAN

Attesting Officer    Commissioner of Patents and Trademarks